United States Patent
Kohn

(10) Patent No.: US 11,089,655 B1
(45) Date of Patent: Aug. 10, 2021

(54) SAFETY CIRCUITS FOR ELECTRIC HEATING ELEMENT

(71) Applicant: Gabriel S. Kohn, Boca Raton, FL (US)

(72) Inventor: Gabriel S. Kohn, Boca Raton, FL (US)

( * ) Notice: Subject to any disclaimer, the term of this patent is extended or adjusted under 35 U.S.C. 154(b) by 37 days.

(21) Appl. No.: 16/709,469

(22) Filed: Dec. 10, 2019

Related U.S. Application Data

(60) Provisional application No. 62/784,321, filed on Dec. 21, 2018.

(51) Int. Cl.
 *G05B 19/042* (2006.01)
 *H05B 1/02* (2006.01)

(52) U.S. Cl.
 CPC .............. *H05B 1/02* (2013.01); *G05B 19/042* (2013.01); *G05B 2219/25252* (2013.01)

(58) Field of Classification Search
 CPC ................ H05B 1/02; G05B 19/042; G05B 2219/25252
 USPC ......................................................... 700/300
 See application file for complete search history.

(56) References Cited

U.S. PATENT DOCUMENTS

| | | | |
|---|---|---|---|
| 5,770,836 A * | 6/1998 | Weiss ................... | H05B 1/0272 219/212 |
| 9,148,911 B2 | 9/2015 | Kohn | |
| 10,164,421 B1 | 12/2018 | Kohn | |
| 2002/0060894 A1* | 5/2002 | Horibata ................ | H03K 17/18 361/100 |
| 2013/0015174 A1* | 1/2013 | Kohn ..................... | H05B 3/342 219/209 |
| 2013/0134149 A1* | 5/2013 | Weiss .................... | H05B 3/146 219/481 |

\* cited by examiner

*Primary Examiner* — Kenneth M Lo
*Assistant Examiner* — Michael W Choi
(74) *Attorney, Agent, or Firm* — Lawrence J. Shurupoff

(57) ABSTRACT

A system controller such as a microprocessor receives voltage signals produced from a resistor identifying the functional or nonfunctional operating state of a power switch which controls the amount of power provided to a load in an electrical system. The resistor is also used to provide voltage signals representing the temperature of a heating element of the type used in heating pads and heating blankets. The functional or nonfunctional operating state of a safety switch in a safety circuit capable of blowing a fuse and cutting power to the load is periodically tested to ensure the safety of the electrical system.

8 Claims, 3 Drawing Sheets

SAFETY CIRCUITS FOR ELECTRIC HEATING ELEMENT

BACKGROUND AND SUMMARY

This disclosure describes circuits and associated software algorithms that help prevent safety-related thermal events such as overheating in electrically-heated products and particularly in heated pads and heated blankets.

Electronically-controlled products such as heating pads, heating wraps, heating blankets and the like that use household electricity as the source of power utilize an electronic power switch or "main power switch" that applies electric power to loads posing potential safety issues. Such loads include heating elements such as heating wires provided within heating pads and heating blankets.

In the case of electrically-heated products, the power is provided on an as needed basis and as directed by a microprocessor to maintain desired temperatures selected by a user. The main power switch turns on and off at varying intervals to produce and maintain a temperature level selected by a user. In practical terms, an electronic power switch as described herein can take the form of, for example, a triac or SCR.

To protect a user from thermal burns, it is critical that the main electronic power switch that controls the temperature of a heating product turns OFF when required in order to maintain a selected temperature and to prevent a potential thermal overheat condition. This is particularly important in those heating products which apply relatively high wattage to a heating element to quickly bring the heating product up to a temperature selected by a user.

To prevent an overheat condition or "thermal runaway", a disabling circuit is provided to disconnect the electronic controls and heating elements from their power source in order to stop all heating when it is determined that the main electronic power switch fails to shut OFF when commanded to do so by a processor control system. This test of the disabling circuit can be carried out first as there is little point to testing the electronic main power switch if it is determined that it has failed but power to the heating element can't be terminated by the disabling circuit.

As described below, improvements over existing heating control systems include:

1. The virtual prevention of a false positive indication of failures of heating control circuits. Multiple fault indications during each test period must be present in order to prevent "false positive" results by any one of two tracked fault conditions. This eliminates the possibility that a perfectly good heating product will be destroyed or forced to discontinue operations unnecessarily.

2. The introduction of dwell time. A dwell time is introduced prior to the initiation of tests in order to allow the power lines to stabilize and for electrical transients to decay, thereby creating a more reliable background for the tests and associated results.

3. A test to determine that a disabling circuit is functional. A disabling circuit is provided to render a heated product such as a heated textile inoperable by blowing a fuse in the event that the main electronic switch, which controls power to a heating element, does not turn OFF when commanded. To ensure that the disabling circuit is capable of blowing the fuse, a test circuit and an associated test are provided in this disclosure to verify the proper operation of the disabling circuit.

Tests for two (2) fault conditions are integrated into a safety test period that is repeated throughout the operation of an electric powered product such as a heating product. These tests are listed as follows:

1. Test the disabling circuit to validate that it operates properly.
2. Test and determine whether the main power switch can turn OFF.

As noted above, an electronic power switch or "main power switch" as described herein can take the form of, for example, a triac or SCR, but other types of switches can be used.

DESCRIPTION OF REPRESENTATIVE EMBODIMENTS

Figure 1:
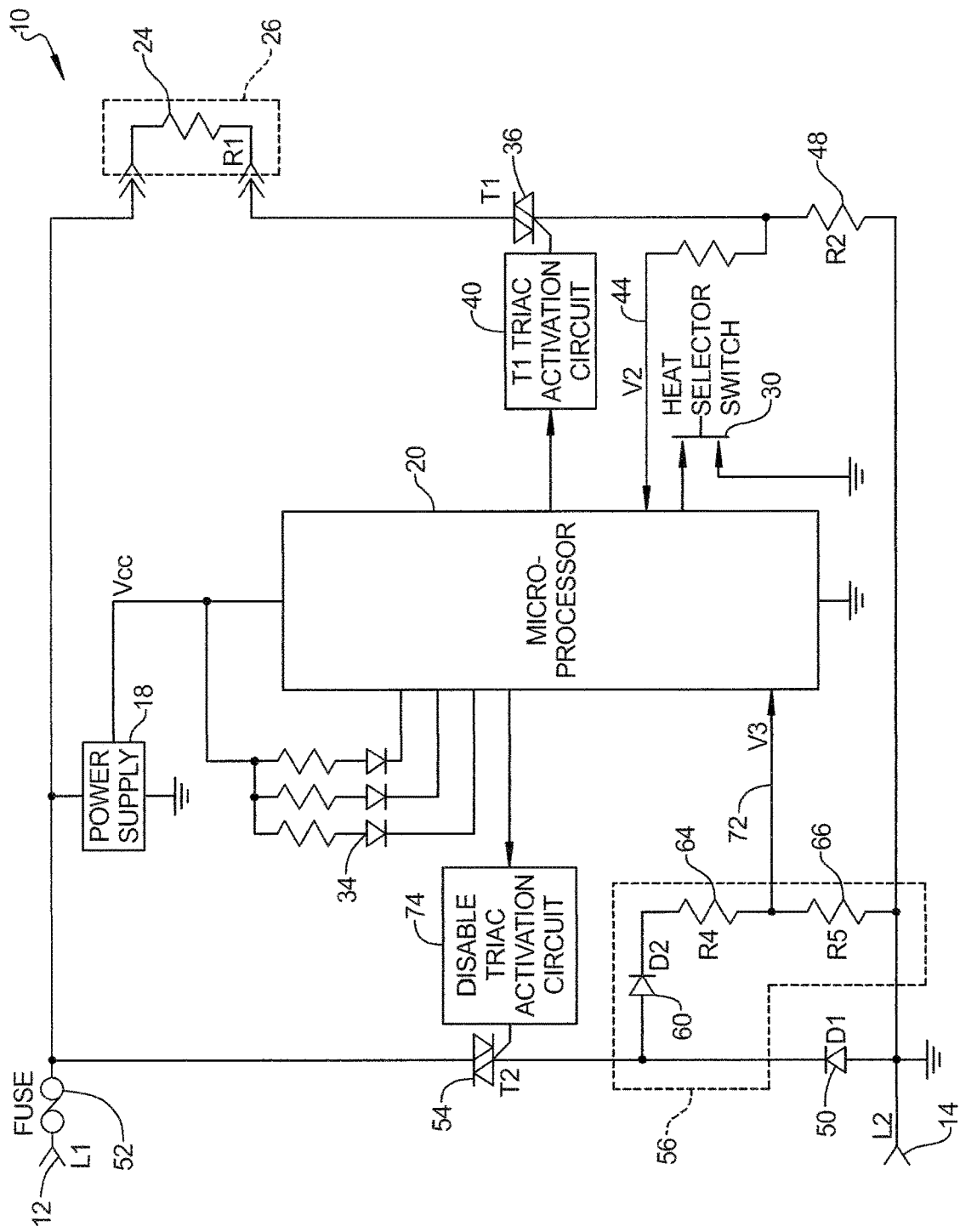
FIG. 1 is a schematic circuit diagram of an example of a processor-controlled heating system constructed in accordance with this disclosure.

An example of a safety system constructed in accordance with this disclosure is shown in FIG. 1. This system can be used with any type of electrical load such as electrically-powered products which generate heat. In the example of FIG. 1, the safety system outlined above is applied to a heating system such as the resistive heating system 10. A power source, such as household alternating current is provided through power lines 12 and 14 to power the heating system 10.

A power supply 18 provides direct current to a processor such as microprocessor 20. Microprocessor 20 controls the operation of the heating system 10, including the operation and testing of the safety circuits described below.

AC power is applied to a resistive load such as a resistive heating element 24 to provide heat to a heating product such as a heating pad 26. The heating element 24 can take the form of a resistive heating wire R1. A user selects a desired level of heat by operating a heat selector switch 30. A series of LEDs 34 lights up sequentially to indicate the level of heat selected.

The level of heat produced by the heating element 24 is controlled by the microprocessor 20 operating a main power switch 36. In this example, the main power switch 36 is shown as a triac T1. Under normal operating conditions, the microprocessor 20 instructs a switch activation circuit 40 to open and close the main power switch 36 (triac T1) according to programmed duty cycles corresponding to heating levels selected by a user.

The microprocessor 20 also receives a signal 44 produced between the main power switch 36 and ground representing the operating temperature of the heating element 24. A voltage drop across a sensor such as resistor 48 (R2) varies inversely with the temperature of the heating element 24 and is sent to the microprocessor as a voltage signal V2. The microprocessor compares the value of this signal, namely the value of V2, with an acceptable heating level set within the microprocessor.

In the event the microprocessor 20 detects an overheated heating element 24 due to V2 falling below a preset value, the microprocessor 20 commands the switch activation circuit 40 to open the main power switch 36 based on the voltage signal 44 produced by sensor 48. The sensor 48 is also used to test the operation of the main power switch 36, as described more fully below.

The microprocessor 20 also operates a system disabling circuit which includes a fuse 52, a safety switch 54 and a diode 50 or D1. In this example, safety switch 54 is represented by a triac T2. The operational condition or state of the safety switch 54 (that is whether the safety switch 54 opens and closes upon commands from the microprocessor 20) is determined by a test circuit 56 which includes a diode 60 or D2 and a first resistor 64 or R4 and a second resistor 66 or R5.

The test circuit 56 produces a test signal 72 in the form of a voltage V3 which serves as an input to the microprocessor 20. Depending on the value of V3, the microprocessor 20 may turn off power to the heating element 24 by commanding, the main power switch 36 to open and stay open.

As further shown in FIG. 1, resistor R2 is used to measure the current through the heating element 24 in the heating pad 26 and through the main power switch 36 (T1) and provide input signals to the microprocessor 20 in the form of voltage inputs V2. These measurements are taken under different operational states of the safety system 10 and serve two different purposes.

During normal operations, the voltage drop V2 across R2 decreases substantially linearly and inversely as the temperature of the heating element 24 in the heating pad 26 increases linearly. This signal, V2, when decreasing below a preset value stored in the microprocessor 20, indicates to the microprocessor 20 when an overheated heating element condition has occurred. At this point the microprocessor 20 stops all heating by opening the main power switch (T1) via the switch activation circuit 40 and keeps the main power switch open until the temperature of the heating element 24 returns to allowable levels.

Resistor R2 also provides a different signal via V2, to determine if the main power switch 36 (T1) has failed to shut off when commanded to do so by the microprocessor 20.

The microprocessor 20 is programmed to carry out testing of the operational states of T1 and T2 during test periods which can be spaced apart such as described below. During each test period the following processes are followed:

1. To help ensure stable and accurate test results, a dwell time of about 200 milliseconds is provided after commanding T1 to open or turn off and before tests can begin. This allows the power lines 12 and 14 and associated circuits to stabilize following any line transients due to activation/deactivation of power to the load (the heating element 24).

2. At some fixed or variable intervals between one second and 30 minutes, for example every 2 minutes, the microprocessor 20 commands the main power switch T1 to turn power off prior to initiation a of test cycle. This period of this test cycle is generally less than 1 second in length.

3. During this test cycle, a series of spaced or staggered tests are conducted to validate the operation of the disabling circuit and the ability of the main power switch 36 (T1) to turn off when so commanded by the microprocessor 20.

4. Two flag registers, one for each type of test are set in the microprocessor memory and are used to record all test results.

The first test: Test the disabling circuit:

After the initial dwell time and during the time that the AC power line L1 is positive relative to the AC power line L2, the microprocessor 20 turns on safety switch 54 (T2 the disabling triac).

If triac T2 is operating properly, it will turn ON and current will flow through T2, D2, R4 and R5 as referenced in FIG. 1. That will result in a voltage signal (marked V3) across R5. The microprocessor 20, upon receiving a detectable V3 voltage value, will then consider T2 to be operable and capable of closing upon command. R4 is set at a high resistance level value to limit the current through the fuse 52 and prevent the fuse 52 from blowing.

If no voltage appears across R5 during the initial test of T2, the microprocessor 20 will consider that T2 failed to turn on, and a flag will be set in the disabling circuit register. In either case the microprocessor 20 will then proceed to retest T2 in the same manner after a predetermined time period such as 100 milliseconds to 200 milliseconds. That is, this initial test is conducted at least twice during each test cycle.

The second test: Test the main power switch (T1):

The test circuit for T1 includes resistor R2. Resistor R2 measures the current through the heating element 24 in the heating pad 26 and through the main power switch (T1), and serves two purposes. During normal operations, the voltage drop V2 across resistor R2 linearly decreases as the temperature of the heating element 24 linearly increases.

This signal 44, which is input to the microprocessor 20 as voltage signal V2, indicates to the microprocessor 20 whether the heating element 24 is functioning properly or overheating. If V2 falls below a set value indicating overheating, the microprocessor 20 commands T1 to turn off and provides an indication to the user that the system 10 has been disabled. Once the heating element 24 cools down, the system 10 may be turned on once again. This is preferable to blowing the fuse 52 which prevents any further use of the system 10.

To test the operation and proper function of T1, the microprocessor 20 also measures the voltage across R2 (marked V2) while T1 is commanded by the microprocessor 20 to turn off via switch activation circuit 40. If NO voltage appears across R2, then the main power switch (T1) is OFF, as commanded prior to the first test above. This indicates that the microcontroller 20 can maintain proper operation of the system 10 and prevent overheating of the heating element 24.

If however, there is a voltage V2 across R2, a flag will set in main switch register. This measurement of V2 is conducted twice during each test cycle with, for example, a period of 100 milliseconds to 200 milliseconds between each test of T1. At the end of each test cycle, ail flags in both registers are cleared.

From a timing perspective, the following tests will be conducted during each test cycle with the power to the heating element 24 turned off by T1 at Time=0.

From 0-199 milliseconds: Dwell time
At 200 milliseconds: Disabling circuit test
At 300 milliseconds: Disabling circuit test
At 400 milliseconds: Main switch test
At 500 Milliseconds: Main switch test The effect on the system 10 as a result of the above tests and during a test period is as follows:

Disabling circuit (T2) tests: A flag is set in the disabling circuit register to indicate that the disabling circuit test detected a suspected problem in this circuit. If more than 1 such flag is set during the test cycle, the microprocessor 20 issues a command to T1 to turn off all heating and annunciate to the user that a system problem has been detected. Otherwise, reset the disabling circuit flag register.

Test Results:

| DIASBLING CIRCUIT TEST RESULTS | CONCLUSION | ACTION |
|---|---|---|
| No flags set | No problems found | Continue operation |
| One flag is set | Assume 1 "false positive" test result | Continue operation |
| 2 flags are set | The disabling circuit is non functional | Stop heating, annunciate a problem to the consumer. |

Main Power Switch (T1): A flag is set in the main power switch register to indicate a suspected shorted main power switch 36 (T1) every time the main power switch (T1) is tested (commanded to open or turn off) and a voltage V2 is measured across R2. If only one flag is set during a test cycle, the main power switch register is cleared.

Test results:

| T1 TEST RESULTS | CONCLUSION | ACTION |
|---|---|---|
| No flags set | No problems found | Continue operation |
| One flag is set | Assume 1 "false positive" test result | Continue operation. |
| 2 flags are set | T1 is shorted | Blow the fuse |

The fuse 52 is blown when the AC cycle is such that power line L2 is positive relative to L1 and when triac T2 is activated via the system disable activation circuit 74. This creates a short circuit across the power lines L1 and L2 via diode D1 and T2 and the fuse 52 thereby blowing the fuse 52.

Figure 2A:
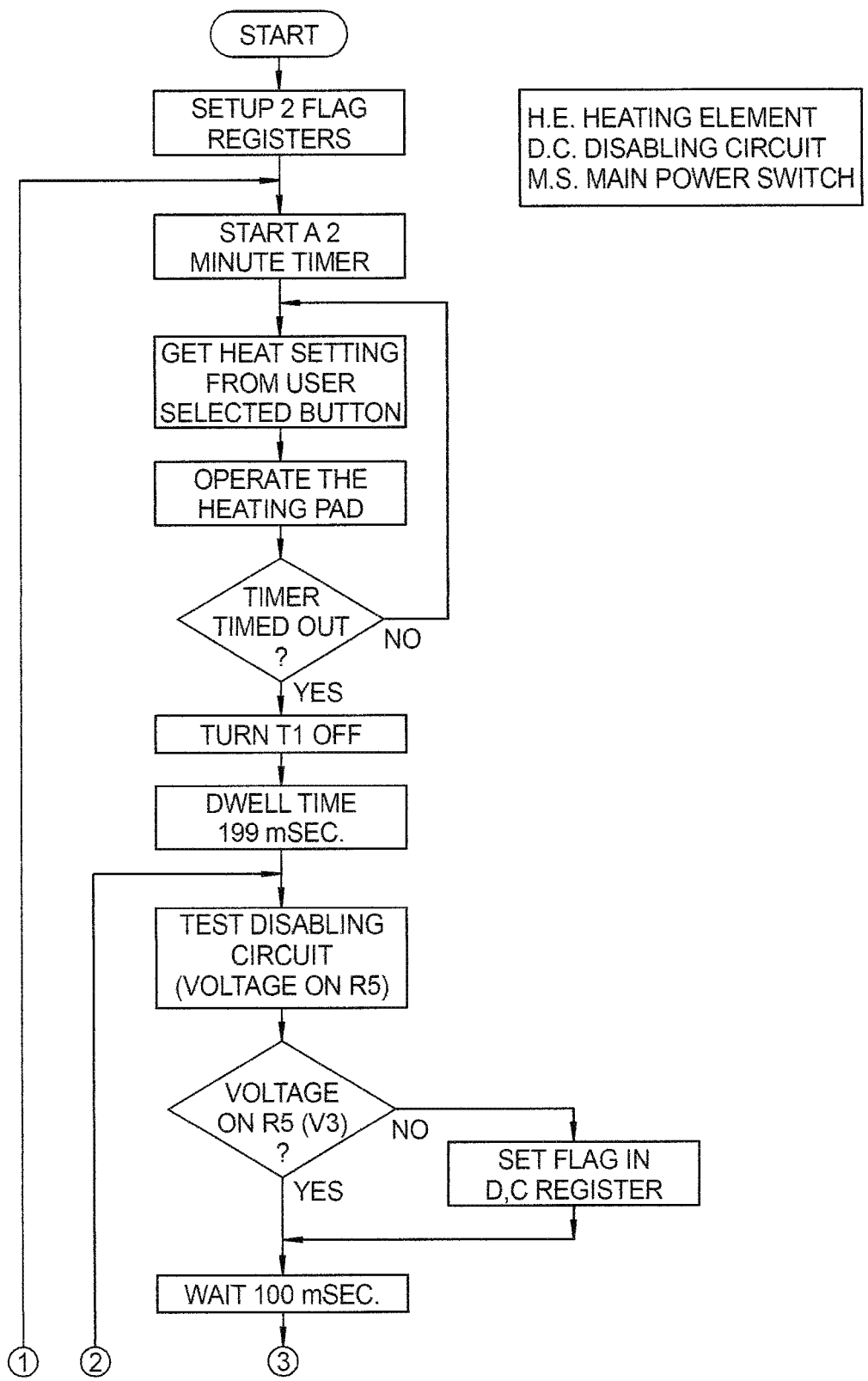
FIGS. 2A and 2B show an example of a logic flow chart or algorithm detailing the operation of the processor-controlled heating system of FIG. 1.
Figure 2B:
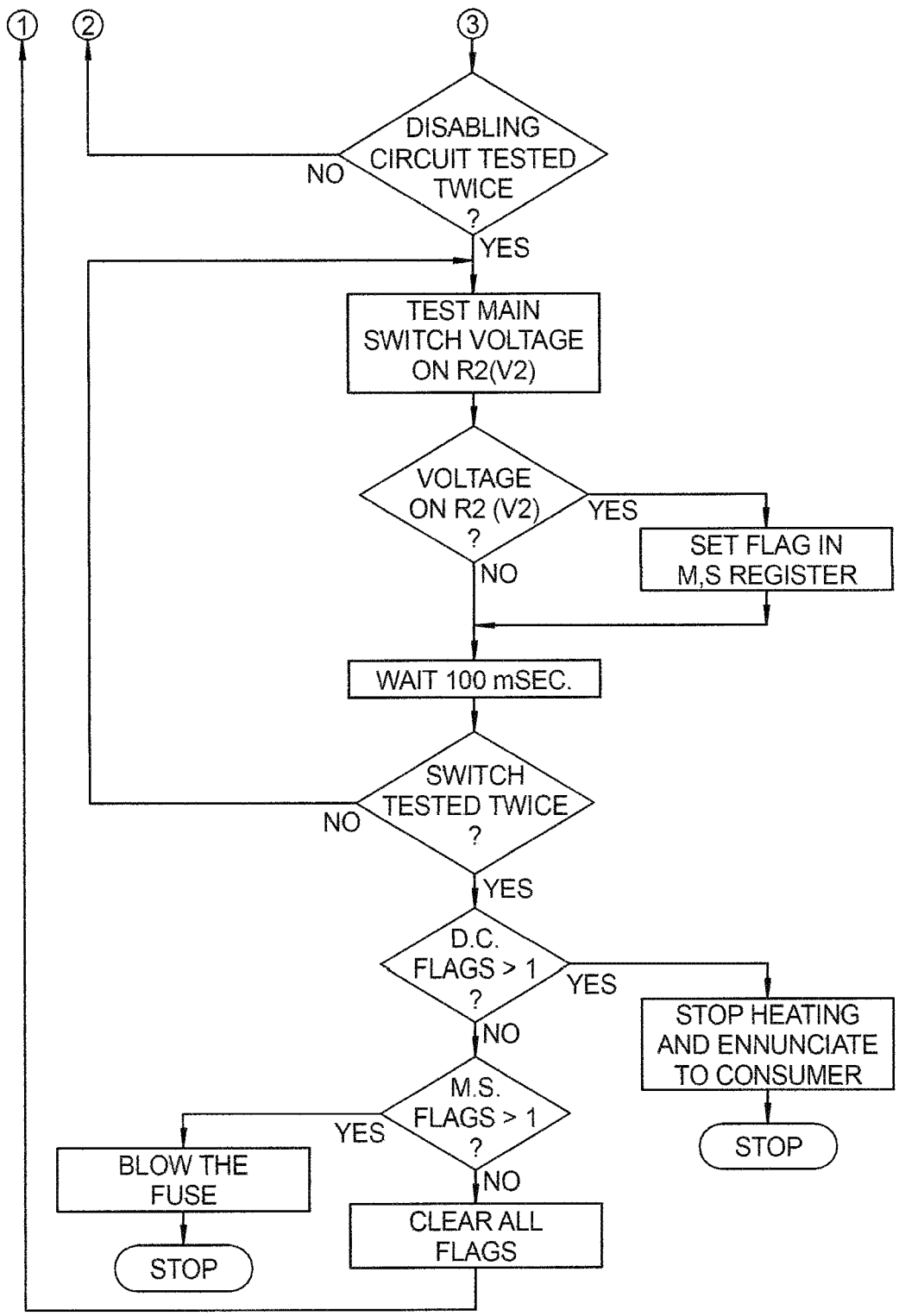

An example of a logic flow chart for operating the microprocessor 20 and controlling the system 10 is shown in FIG. 2. This flow chart includes the measuring and testing of the system 10 as described above and is self-explanatory.

There has been disclosed heretofore the best embodiment of the disclosure presently contemplated. Obviously, numerous modifications and variations of the present disclosure are possible in light of the above teachings. It is therefore to be understood that within the scope of the appended claims, the disclosure may be practiced otherwise than as specifically described herein.

What is claimed is:

1. A heating system, comprising:
   a microprocessor;
   a heating element;
   a power switch opening and closing as directed by said microprocessor to control temperature of said heating element;
   a disabling circuit comprising a system disabling switch and a fuse, said fuse, when blown open, cuts power to said heating element;
   a test circuit providing signals to said microprocessor indicating whether or not said system disabling switch is operational; and
   wherein said microprocessor commands said power switch to open and remain open upon said microprocessor receiving a signal from said test circuit indicating said system disabling switch is not operating as commanded by said microprocessor.

2. The system of claim 1, wherein said test circuit comprises a first diode and first and second resistors providing said signals to said microprocessor.

3. The system of claim 2, further comprising a second diode arranged in a parallel circuit with said first diode and said first and second resistors.

4. The system of claim 1, further comprising a sensor providing a first signal to said microprocessor indicating whether said power switch is open or closed.

5. The system of claim 4, wherein said sensor further provides a second signal to said microprocessor indicating a temperature of said heating element.

6. The system of claim 1, further comprising a heating pad or heating blanket and wherein said heating element is provided in said heating pad or said heating blanket.

7. The system of claim 1, wherein said disabling circuit is tested during spaced-apart test cycles.

8. The system of claim 7, wherein said disabling circuit is tested more than once during each of said cycles.

* * * * *